United States Patent
Koster et al.

(10) Patent No.: US 7,267,643 B2
(45) Date of Patent: Sep. 11, 2007

(54) METHOD AND APPARATUS FOR TEMPORARILY INSERTING AND POSITIONING AT LEAST ONE ENERGY EMITTING SOURCE IN AN ANIMAL BODY

(75) Inventors: Albert Dirk Adrianus Koster, Utrecht (NL); Frits Van Krieken, Dieren (NL); Hans Martin Schot, Veenendaal (NL)

(73) Assignee: Nucletron B.V., Veenendaal (NL)

( * ) Notice: Subject to any disclaimer, the term of this patent is extended or adjusted under 35 U.S.C. 154(b) by 625 days.

(21) Appl. No.: 10/452,123

(22) Filed: Jun. 3, 2003

(65) Prior Publication Data

US 2004/0034312 A1 Feb. 19, 2004

(30) Foreign Application Priority Data

Jun. 3, 2002 (NL) .................................... 1020740

(51) Int. Cl.
*A61N 5/00* (2006.01)
*A61M 36/00* (2006.01)
(52) U.S. Cl. .............................................. 600/7; 600/3
(58) Field of Classification Search ................ 600/1–8; 128/897–898; 606/7, 8, 14, 21, 28; 607/92, 607/105, 112, 149
See application file for complete search history.

(56) References Cited

U.S. PATENT DOCUMENTS 4,427,005 A 1/1984 Tener (Continued)

FOREIGN PATENT DOCUMENTS

DE 41 09 205 A1 9/1992

(Continued)

*Primary Examiner*—Samuel G. Gilbert
(74) *Attorney, Agent, or Firm*—Birch, Stewart, Kolasch & Birch, LLP

(57) ABSTRACT

The invention relates to a method and apparatus for temporarily inserting and positioning at least one energy emitting source in an animal body, wherein the apparatus comprises at least: a hollow open needle having a proximal needle end and a distal needle end to be inserted into the body, so as to provide a channel in the body; a guide tube having a proximal guide tube end and a distal guide tube end to be inserted into the hollow open needle; the hollow open needle being retractable from the body over the guide tube; a first fixing element for fixating the guide tube with said proximal guide tube end relative to the body; a catheter tube having a closed distal catheter tube end and an open proximal catheter tube end to be inserted with its distal catheter tube end until a predetermined depth into the guide tube and the body via said proximal guide tube end and fixating the catheter tube to the guide tube; at least one energy emitting source for insertion into the catheter tube via said proximal catheter tube end and, which at least one energy emitting source is removed after a predetermined period of time from the catheter tube.

According to the invention the hollow open needle and said guide tube are inserted through a part of said body leaving both proximal and distal ends of said guide tube exposed outside either sides of said part of said body, and a second fixing element for fixing the guide tube with said distal guide tube end relative to the body.

29 Claims, 6 Drawing Sheets

U.S. PATENT DOCUMENTS

| | | | |
|---|---|---|---|
| 4,580,561 A | | 4/1986 | Williamson |
| 4,682,593 A | | 7/1987 | Johnson |
| 4,763,671 A | | 8/1988 | Goffinet |
| 4,969,863 A | * | 11/1990 | van't Hooft et al. ............ 600/3 |
| 4,976,680 A | * | 12/1990 | Hayman et al. ................ 600/7 |
| 6,251,060 B1 | | 6/2001 | Hooft et al. |
| 6,572,525 B1 | * | 6/2003 | Yoshizumi ..................... 600/7 |
| 2004/0116767 A1 | * | 6/2004 | Lebovic et al. ................. 600/7 |

FOREIGN PATENT DOCUMENTS

| | | |
|---|---|---|
| EP | 0 366 214 A2 | 5/1990 |
| EP | 0 576 101 A1 | 12/1993 |
| EP | 0 791 374 A2 | 8/1997 |
| WO | WO98/40032 A1 | 9/1998 |

* cited by examiner

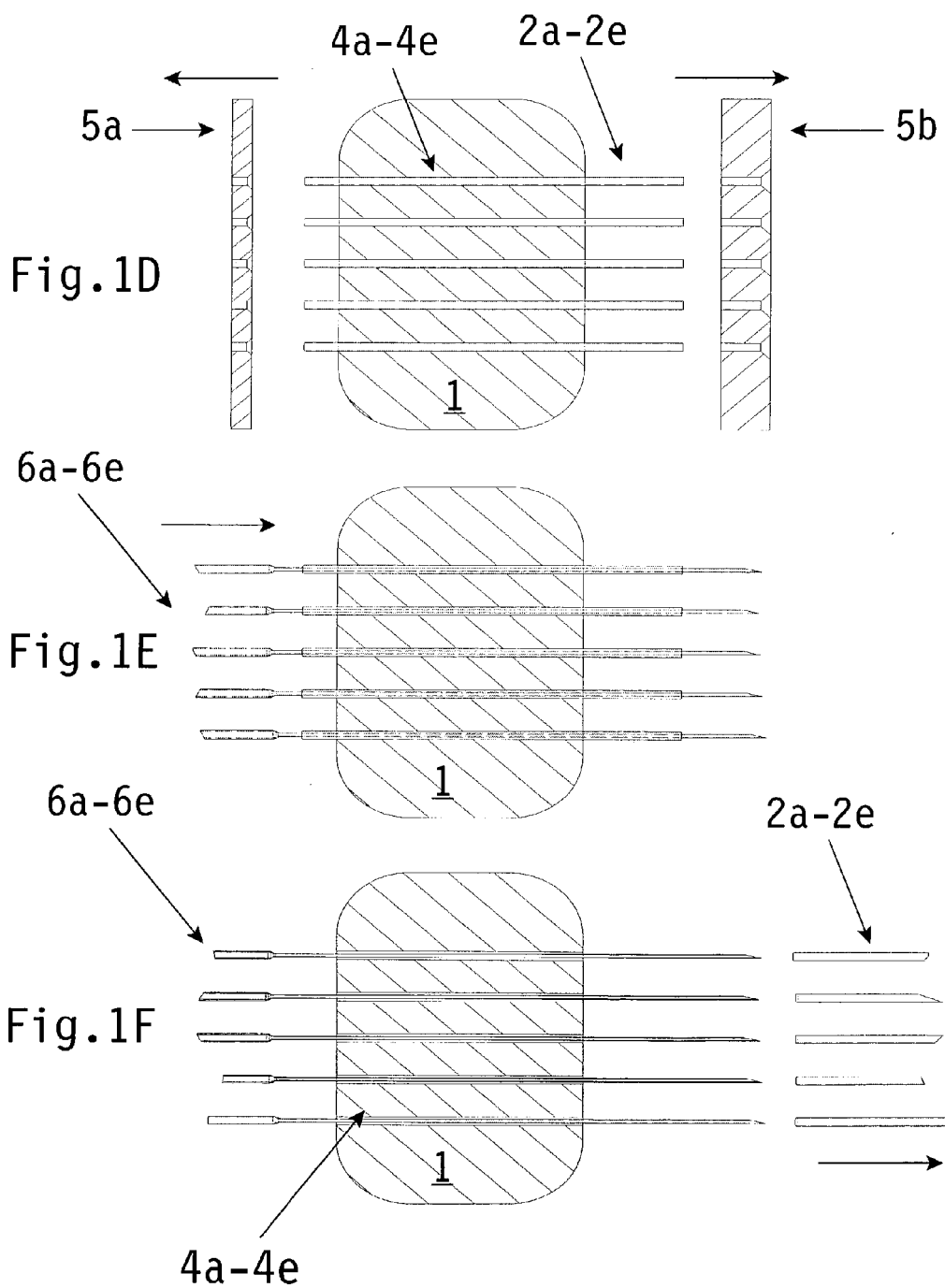

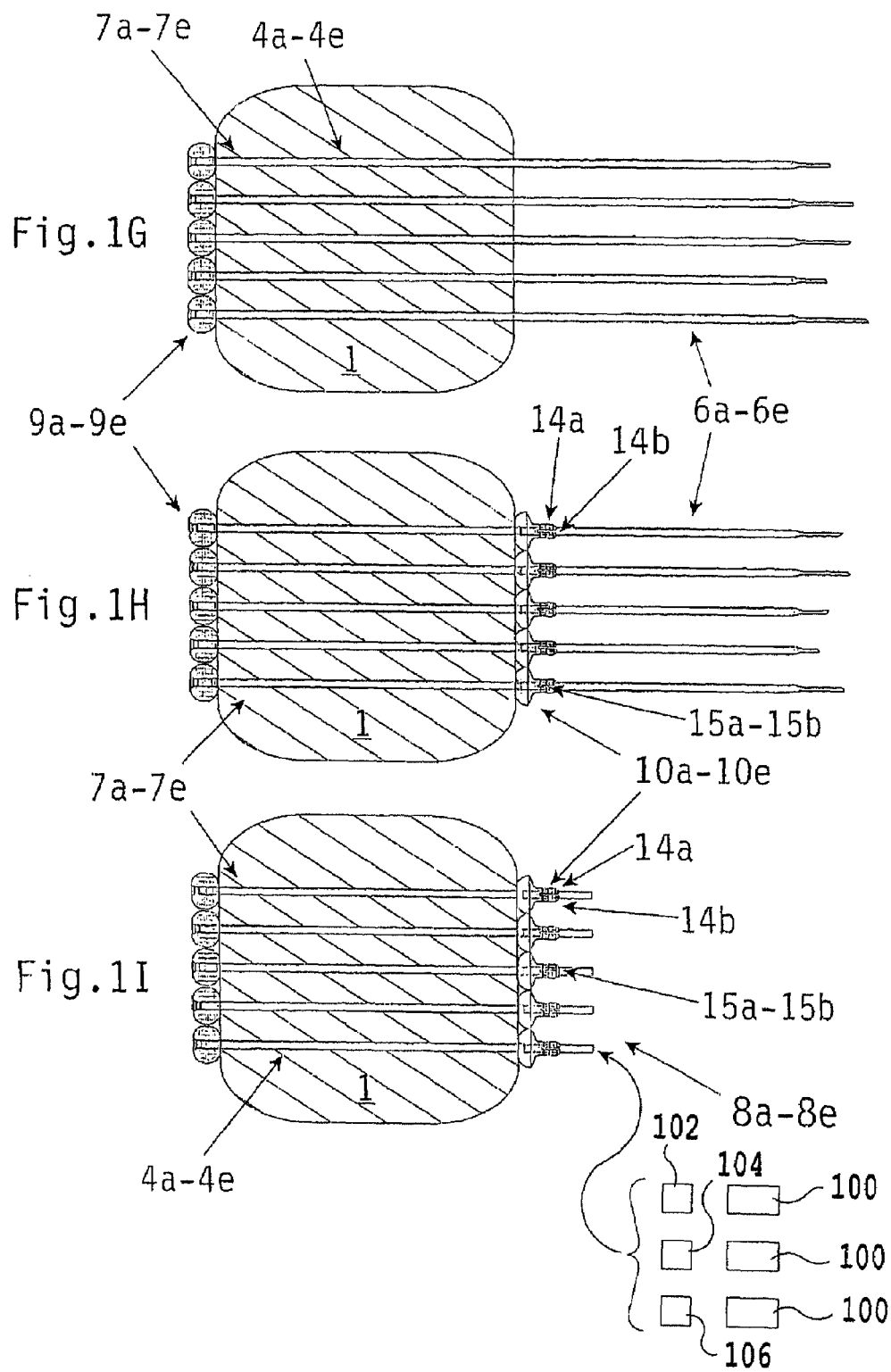

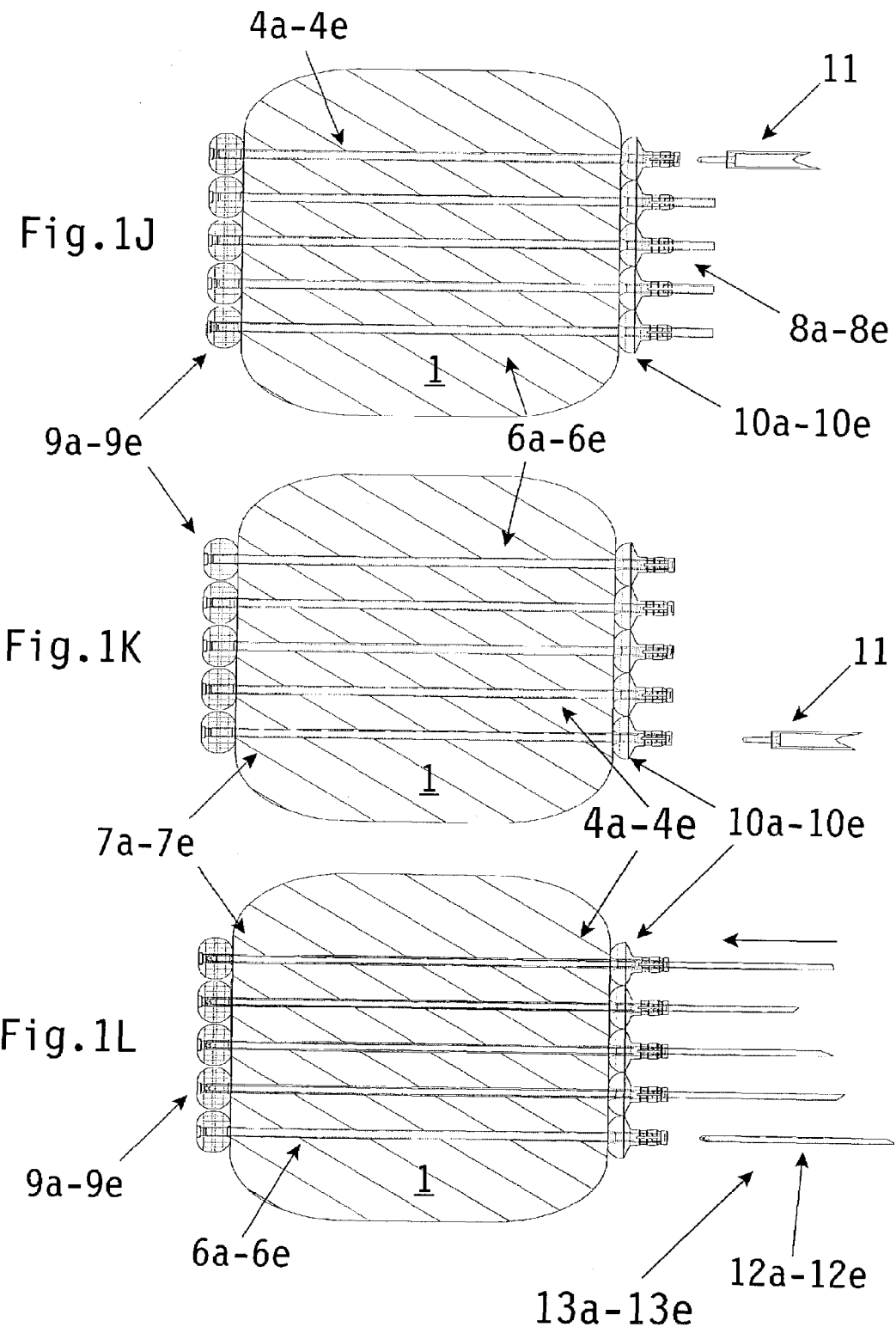

METHOD AND APPARATUS FOR TEMPORARILY INSERTING AND POSITIONING AT LEAST ONE ENERGY EMITTING SOURCE IN AN ANIMAL BODY

The invention relates to a method for temporarily inserting and positioning at least one energy emitting source in an animal body comprising at least the steps of:

A inserting at least one hollow open needle having a proximal needle end and a distal needle end into the body so as to provide at least one channel in the body;

B inserting a guide tube having a proximal guide tube end and a distal guide tube end to be inserted into the hollow open needle;

C retracting the hollow open needle over the guide tube out of the body, while pulling the guide tube in position in the channel in the body;

D fixating the guide tube with said proximal guide tube end relative to the body;

E inserting via said proximal guide tube end a catheter tube having a closed distal catheter tube end and an open proximal catheter tube end with its distal catheter tube end until a predetermined depth into the guide tube and the body and fixating the catheter tube to the guide tube;

F inserting via said proximal catheter tube end at least one energy emitting source into said catheter tube, and G after a predetermined period of time removing the at least one energy emitting source from the catheter tube.

The invention relates moreover to an apparatus for temporarily inserting and positioning at least one energy emitting source in an animal body comprising at least:

A a hollow open needle having a proximal needle end and a distal needle end to be inserted into the body, so as to provide a channel in the body;

B a guide tube having a proximal guide tube end and a distal guide tube end to be inserted into the hollow open needle;

C the hollow open needle being retractable from the body over the guide tube;

D a first fixing element for fixating the guide tube with said proximal guide tube end relative to the body;

E a catheter tube having a closed distal catheter tube end and an open proximal catheter tube end to be inserted with its distal catheter tube end until a predetermined depth into the guide tube and the body via said proximal guide tube end and fixating the catheter tube to the guide tube;

F at least one energy emitting source for insertion into the catheter tube via said proximal catheter tube end and, G which at least one energy emitting source is removed after a predetermined period of time from the catheter tube.

In the process of brachytherapy a radioactive source is brought to the vicinity of cancerous tissue for irradiating that cancerous tissue with radioactive radiation. Numerous proposals have been made for devices to carry out such processes. Such processes are e.g. known as manual low dose rate brachytherapy using wires, seeds, pellets, tubes and high dose rate or remote afterloading HDR brachytherapy. In LDR and HDR brachytherapy one or more low and high, respectively, intensity radioactive sources are fixed at a distal end of a so-called guide wire, i.e. remote afterloading. For certain types of cancer e.g. prostate cancer or breast cancer, more than one time spaced apart dose of radiation is required to be effective. Those doses are given over a period of several days. A patient has to be hospitalized during that period. Each time a dose is to be delivered during that period needles are placed into the body of the patient and treatment started. It is also known to have the needles remain in the body. Especially HDR brachytherapy needs only a few minutes or less for one dose. Thus for a patient such method means a long time in the hospital for a few short time treatments. Patients perceive such a method as being quite burdensome.

It is known in brachytherapy to insert a number of needles in a body semi-permanently for the total duration of the treatment. In that case a number of needles is inserted into the body, usually by means of a template, and fixed relative to the body by means of a fixing element. The template may also function as a fixing element. Each of the needles then is provided with a coupling. All needles stick out of the body for a certain distance and are provided with a coupling. Through the couplings so-called guide tubes or transfer tubes can be connected to the needles. As is well known in brachytherapy a so-called afterloader machine may be used to control the transport of the radiation source from the machine to the needles through the guide tubes or transfer tubes. An afterloader machine therefore is provided with an indexer device. The guide tubes or transfer tubes with ends thereof coupled to the fixing element are in turn coupled at opposite ends to the indexer. As is well known from afterloader brachytherapy machines manufactured and sold by e.g. Nucletron B. V. from the Netherlands a radioactive source at a distal tip of a so-called guide wire is transported under control of the machine from a safe in the machine through the indexer into a guide tube and through the guide tube into a corresponding needle. After a certain period the wire with the radioactive source is retracted into the afterloader machine. In case a further irradiation is to take place from another needle, the indexer is controlled such that a further guide tube is connected to receive the wire with the radioactive source at the tip. And so on until all required irradiations have taken place from the various needles. Then the needles are disconnected from the guide tubes. The patient then is "free" to walk around with a set of needles in his or her body until the next treatment has to take place. It is known to use plastic needles that have a small amount of flexibility instead of inflexible metal needles. The above description relates also to such flexible plastic needles.

During the periods that no treatment is taking place the patient is free in theory to walk around, however, in practice the set of needles or flexible tubes sticking out of the body prevents the patient to feel really free.

A method and an apparatus according to the above mentioned preambles are disclosed in U.S. Pat. No. 6,251,060-B1 granted to the applicant of this application.

In U.S. Pat. No. 6,251,060-B1 a radioactive source is inserted into a guide tube present in a body by means of a needle, which needle is fixed with one end to the skin of the body using additional measures, like adhesive tape and a fixing element. The other end of the insertion needle is inserted until a certain depth into the body depending on the radiation therapy treatment. In order to obtain a proper fixation or positioning of the radioactive source inside the body, the guide tube or guide sheath is partly collapsible under pressures exerted by the body tissue on the sheath. The non-collapsible end part of the guide sheath present in the body acts as an anchoring device for the radioactive source present in the closed end of the sheath inside the body.

In order to support the above complicated insertion process of a radioactive source into the body the closed end of the guide sheath present in the body is provided with a radiopaque marker for controlling the exact positioning of the sheath inside the body using known imaging means.

Apart from the complex parts for connecting the guide sheath to the skin of the patient's body, the method and apparatus according to U.S. Pat. No. 6,251,060-B1 suffer from problems concerning the exact positioning of the energy emitting source within the guide sheath inside the body, as the guide sheaths are only connected at one side to the skin of the body and are subjected to a displacement of the other closed end inside the body relative to the cancerous tumour to be treated.

Hence the method and apparatus for temporary inserting and positioning a radioactive source in an animal body according to U.S. Pat. No. 6,251,060-B1 are not useful for temporarily inserting and exactly positioning a radioactive source during subsequent radiation therapy treatment sessions for performing radiation therapy treatments under the same parameters. Moreover, the known method and apparatus are not suited for temporarily inserting and positioning a energy emitting source in a rather quick manner, without discomforting the patient.

Moreover, the known method and apparatus according to U.S. Pat. No. 6,251,060-B1 are not suited for the use of high dose rate energy emitting sources (HDR-sources) due to the undesirable exposure to radiation of the skin and body tissue next to the cancerous tumour.

The present invention aims to prevent the above-described problems and aims to provide a method and apparatus for temporarily inserting and positioning at least one energy emitting source in an animal body, which method is further characterised by the at least one hollow open needle inserted at step A and said guide tube inserted at step B are inserted through a part of said body leaving both proximal and distal ends of said guide tube exposed outside either sides of said part of said body, and I fixing the guide tube with said distal guide tube end relative to the body.

The apparatus according to the invention is characterised in that the hollow open needle and said guide tube are inserted through a part of said body leaving both proximal and distal ends of said guide tube exposed outside either sides of said part of said body, and a second fixing element for fixing the guide tube with said distal guide tube end relative to the body.

By exposing both proximal and distal ends of said guide tube outside both sides of the body and fixing both guide tube ends, a proper fixation of the guide tube relative to the body is obtained, thus guaranteeing an exact positioning of the energy emitting source within the guide tube relative to the cancerous tumour to be treated. This exact positioning is maintained during subsequent radiation therapy treatment sessions and due to the two-side fixation of each guide tube relative to the cancerous tumour to be treated no in adverse displacement of the guide tubes can take place, which would lead to a repositioning or relocation of the guide tubes within the body.

According to a further aspect of the invention said energy emitting source is inserted into the catheter tube by means of a flexible wire having a proximal wire end and a distal wire end, wherein said energy emitting source is connected at the distal end of said flexible wire.

More in particular, said catheter tube is connected with said proximal catheter end to an after loader apparatus, wherein the flexible wire is connected with said proximal wire end to energy emitting source drive means of said after loader-apparatus.

This allows the use of multiple radiation therapy treatment sessions wherein energy emitting sources easily can be inserted and retracted via said catheter tube and the guide tube into the body. Hence, only a set of guide tubes have to be inserted inside the body near the cancerous tumour to be treated, which guide tubes have to be connected to the body on both distal and proximal ends, which are exposed outside the body. This, as stated above, not only insures a proper orientation of the guide tubes during the entire radiation therapy treatment but moreover minimizes the discomfort to the patient.

The discomfort to the patient is further minimized while in a further aspect of the apparatus according to the invention the catheter tube is made of a flexible material, like plastic. Thus the flexible catheter tube is well suited in following the curvature of the body, more particular the curvature of the breast and chest of a woman during insertion.

In order to facilitate the subsequent insertion and retraction of the catheter tube into each guide tube during subsequent radiation therapy treatment sessions, said guide tube is non-collapsable between said proximal guide end and said distal guide end.

According to a further aspect according to the invention said distal end of said guide tube has a smaller diameter than the rest of said guide tube. This feature reduces the forming of scars at the skin surface at one side of the body where the guide tubes are exposed outside the body of the patient.

In order to facilitate and in order to obtain a more accurate positioning of the guide tubes relative to the cancerous tumour to be treated according to the invention a template is temporarily placed at either side of said part of the body for positioning both proximal and distal ends of said hollow needle. More in particular, both templates are mounted on one fixture.

According to a further aspect of the apparatus according to the invention the first fixing element has means for fixation to the proximal end of the guide tube, wherein said fixation means comprise two protruding parts extending parallel to each other and separated by two slits.

The mounting of the fixing element on each proximal end of the guide tube is facilitated due to the fact that the two protruding parts are urged away from each other due to the interaction between the slits and the legs of a tweezer-like device.

More in particular each leg of said tweezer-like device is provided with a notch cooperating with each slit.

According to a further aspect of the apparatus according to the invention said treatment device is fastenable to the fixing element by means of a coupling device, wherein the coupling device has one part of a click fit coupling, and another part of the click fit coupling is part of the fixing element, or wherein the coupling device has one part of a pressure and friction coupling and another part of the pressure and friction coupling is a part of the fixing element, or wherein the coupling device is one part of a key and lock coupling and another part of the key and lock coupling is part of the fixing element.

For a proper and accurate connection between the guide tube and the fixing element close to the skin of the body, the guide tube is made of a heat meltable material and the heat melted guide tube adheres to the fixing elements upon cooling in contact therewith.

According to another aspect of the apparatus according to the invention, the energy emitting source is a high dose rate radio active source.

According to another aspect of the apparatus according to the invention the energy emitting source is an activatable energy emitting source, which is operative between an activated and unactivated state, and more in particular the activatable energy emitting source is an X-ray emitting source, a light-emitting device or a radiation emitting source, such as a High Dose Rate, a Pulse Dose Rate or a Low Dose Rate radiation emitting source.

According to a further aspect of the invention a dummy wire is to be inserted in the empty guide tube after the removal of the treatment device, wherein each leg of said tweezer-like device is provided with a notch cooperating with each slit.

Further details, advantages and features of the invention are shown not only in the claims and the features therein, singly and/or in combination, but also in the following description of preferred embodiments shown in the drawing, which drawing discloses, FIGS. 1A–1L show schematically the subsequent steps of the method according to the invention using an embodiment of an apparatus according to the invention;

In FIGS. 1A through 1L a body and more in particular a breast of a woman is indicated by numeral 1. At the location on either sides of the breast where needles are to be inserted templates 5a and 5b can be placed. In order to obtain a proper alignment of the templates 5a and 5b with each other both templates are mounted on a fixture (not shown).

Using the templates 5a–5b or making use of other kinds of alignment indications on e.g. the body 1 one or more (for illustrative purposes only, here five needles 2a–2e are used) open needles 2a–2e, each provided with a trocar needle 3a–3e inside it, are inserted into the body 1 near a cancerous tissue (not shown). Each trocar needle 3a–3e fills up the open needle 2a–2e, so that during insertion into the body a channel, generally 4a–4e (see FIG. 1D), is formed.

Figure 1A:
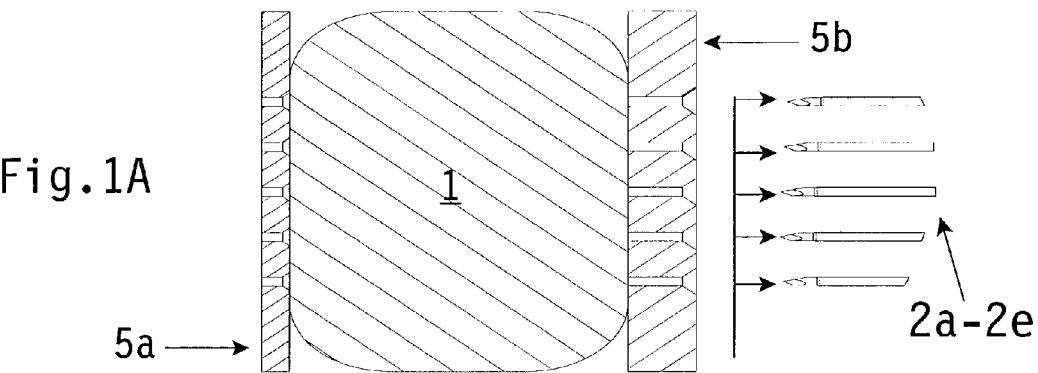
Figure 1B:
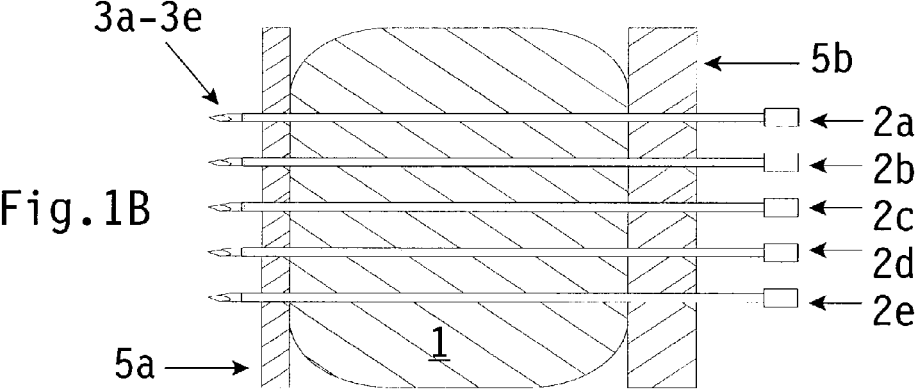
Figure 1C:
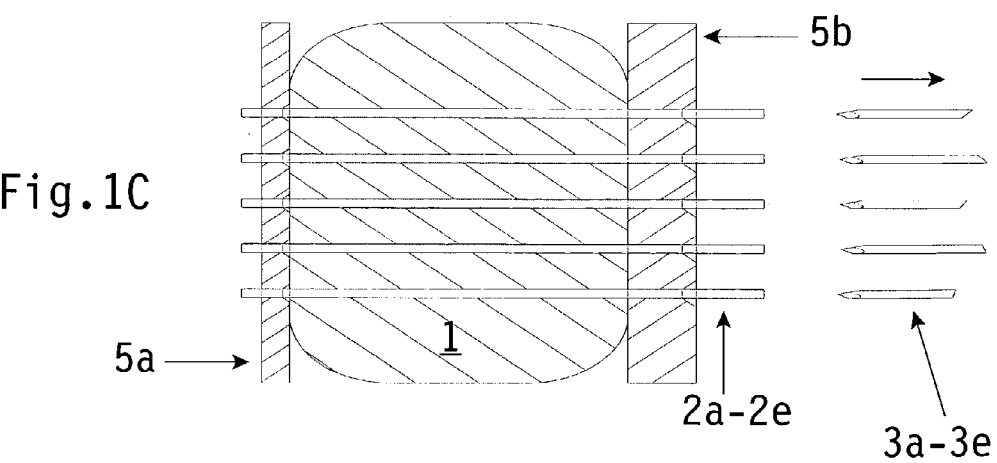

As clearly shown in FIGS. 1A–1C the hollow needles 2a–2e are inserted completely through the part of the body or breast 1 leaving both ends exposed outside either sides of the breast 1.

Subsequently, as shown in FIG. 1C, the trocar needles 3a–3e are retracted. The open needles 2a–2e remain inside the body, retaining the channels 4a–4e. Then as shown in FIG. 1D, both templates 5a–5b are removed.

Next through each open needle 2a–2e guide tubes 6a–6e are inserted. Once the guide tubes 6a–6e are completely inserted through the open needle 2a–2e, thereby leaving both ends of the guide tubes 6a–6e exposed outside either sides of the breast 1. The support given by needles 2a–2e for retaining the channels 4a–4e is no longer required and the open needles 2a–2e are removed from the breast as shown in FIG. 1F and together with the removal of the open needle the guide catheters are pulled in place.

Subsequently, each guide tube 6a–6e is further inserted through the body part (or breast 1) until one closed distal end 7a–7e of the guide tube 6a–6e provided with a fixing element 9a–9e abuts against the skin of the breast 1. This situation is disclosed in FIG. 1G.

Then a further fixing element 10a–10e (see figure 1H) is shifted over the other open proximal end 8a–8e of each guide tube 6a–6e. According to the invention each fixing element is provided with two protruding parts 14a–14b, which extend parallel to each other and which are separated by means of two slits 15–15b (one slit 15a is shown in the FIGS. 1H–1L). These two protruding parts 14a–14b are urged away from each due to the interaction between the slits 15a–15b and the legs of a tweezer-like device (not shown), in order to facilitate the shifting movement of the fixing element 10a–10e over the proximal end 8a–8e of each guide tube.

Once the fixing elements 10a–10e abut against the skin of the breast 1 as shown in FIG. 1H, the two protruding parts 14a–14b are released and due to their resilience they clamp against and around the open proximal 8a–8e end of each guide tube 6a–6e.

In FIG. 1I the proximal ends 8a–8e of each guide tube are cut off until a desired length.

Subsequently the fixing elements 10a–10e and the open proximal ends 8a–8e of each guide tube 6a–6e are connected together, for example by gluing. In a preferred embodiment however the guide tubes 6a–6e are made of a heat meltable plastic material, which material when being brought in a heat melted state by means of the supply of energy using a suitable device 11 can be brought in contact and fixedly connected to the fixing elements 10a–10e after cooling. These steps are shown in FIGS. 1J and 1K.

After the open proximal ends 8a–8e are connected to the fixing elements 10a–10e, the guide tubes 6a–6e are now secured on either sides of the breast 1, thus ensuring a proper fixation of the guide tube for subsequent radiation therapy treatment sessions, without the risk of displacement of the guide tubes inside the body relative to the cancerous tumour to be treated.

Preferably the guide tubes are made of a flexible material, such as plastic, in order to facilitate the patient in his or her daily behaviour during the periods that no treatment is taking place. This means also that the patient is free in theory to walk around outside the hospital as no energy emitting source is present inside the guide tube 6a–6e for a prolonged period of time. The fixing elements 9a–9e and 10a–10e have preferably a spherical shape, which is regarded as patient or user friendly as the skin is less irritated.

For performing a radiation therapy treatment session hollow needles or catheter tubes 12a–12e, each having a closed distal end 13a–13e are inserted into the breast 1 through the guide tubes 6a–6e via the open proximal guide tube ends 8a–8e. Preferably the catheter tubes 12a–12e are each inserted with the closed end 13a–13e until a certain predetermined depth into the guide tube, which insertion depth is separately determined for each catheter tube depending on the location of the cancerous tumour in respect to the guide tubes and the radiation therapy treatment planning parameters, as preplanned by the medical personnel administering the energy emitting sources to the patient.

Inside each hollow catheter tube 12a–12e a number of radioactive pellets, if necessary, separated by non-radioactive spacers is present. The hollow catheter tubes 12a–12e are remaining in place for a time as desired for each radiation therapy treatment session. Then they are retracted and stored elsewhere with the radioactive pellets and the non radioactive spacers still present in it until the next treatment of the same patient.

However the method and apparatus according to the invention are well suited for the use of high dose rate or remote afterloading HDR brachytherapy. With this radiation treatment therapy the catheter tubes 12a–12e are connected with their open proximal catheter ends to an after loader apparatus via the indexer means of said after loading apparatus (not shown). Subsequently a flexible source wire (not shown) is inserted with its distal free end into the catheter tube 12a–12e until the closed distal end 13a–13e of the catheter tube.

Figure 2:
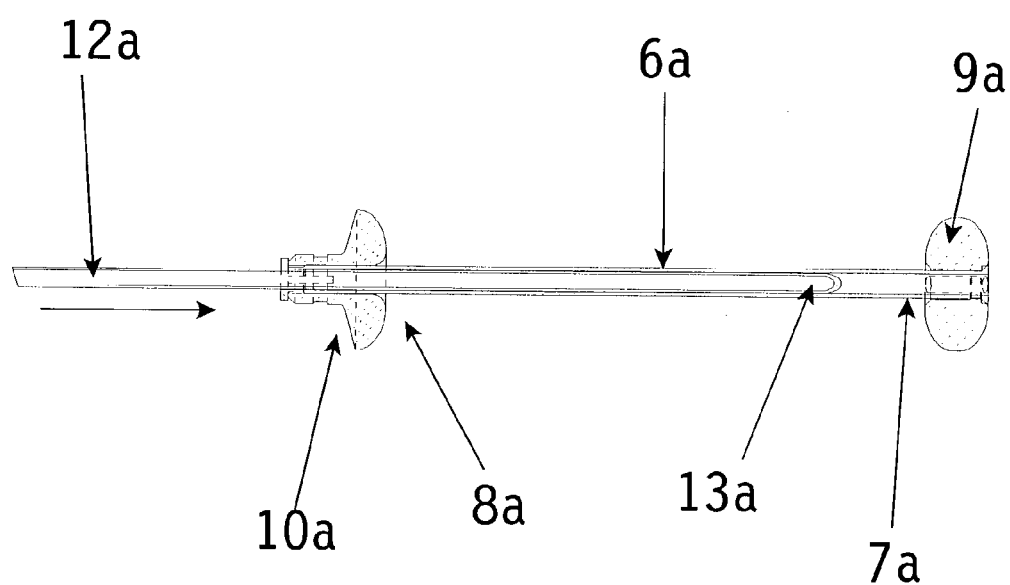
FIG. 2 shows another embodiment of the apparatus according to the invention in more detail.

The flexible wire is therefore connected with its proximal end to the energy emitting source drive means present in the after loader apparatus. With the use of the indexer means and the drive means the flexible wire is guided through one of the several catheter tubes 12a–12e. A energy emitting source is connected to the distal end 13a of the flexible wire and thus also inserted into the catheter tube 12a by the drive means of the after loader apparatus, until the energy emitting source abuts to the closed distal end 13a–13e of the catheter tube 12a–12e. This assures a proper positioning of the energy emitting source inside the breast 1 relative to the cancerous tumour to be treated. See also the detailed view of FIG. 2.

The energy emitting source can be a high dose rate radioactive source (HDR source) or a low dose rate radioactive source (LDR source) depending on the type of radiation therapy treatment session to be performed.

The energy emitting source can also be an activatable energy emitting source, which is operative between an activated and an un-activated state. The activatable radiation emitting device can be an X-ray emitting device and more in particular a miniature X-ray emitting device.

Herewith the radiation dose exposed to both the cancerous tumour to be treated and the skin and healthy body tissue of the patient can be well controlled.

As it is desirable to keep the guide tubes 6a–6e open during the insertion of the catheter tube 12a–12e and the flexible wire with the energy emitting source said guide tube 12a–12e are made of a material, which is flexible and comfortable to the patient, but which material is moreover non-collapsable between the distal and proximal guide ends.

Figure 3:
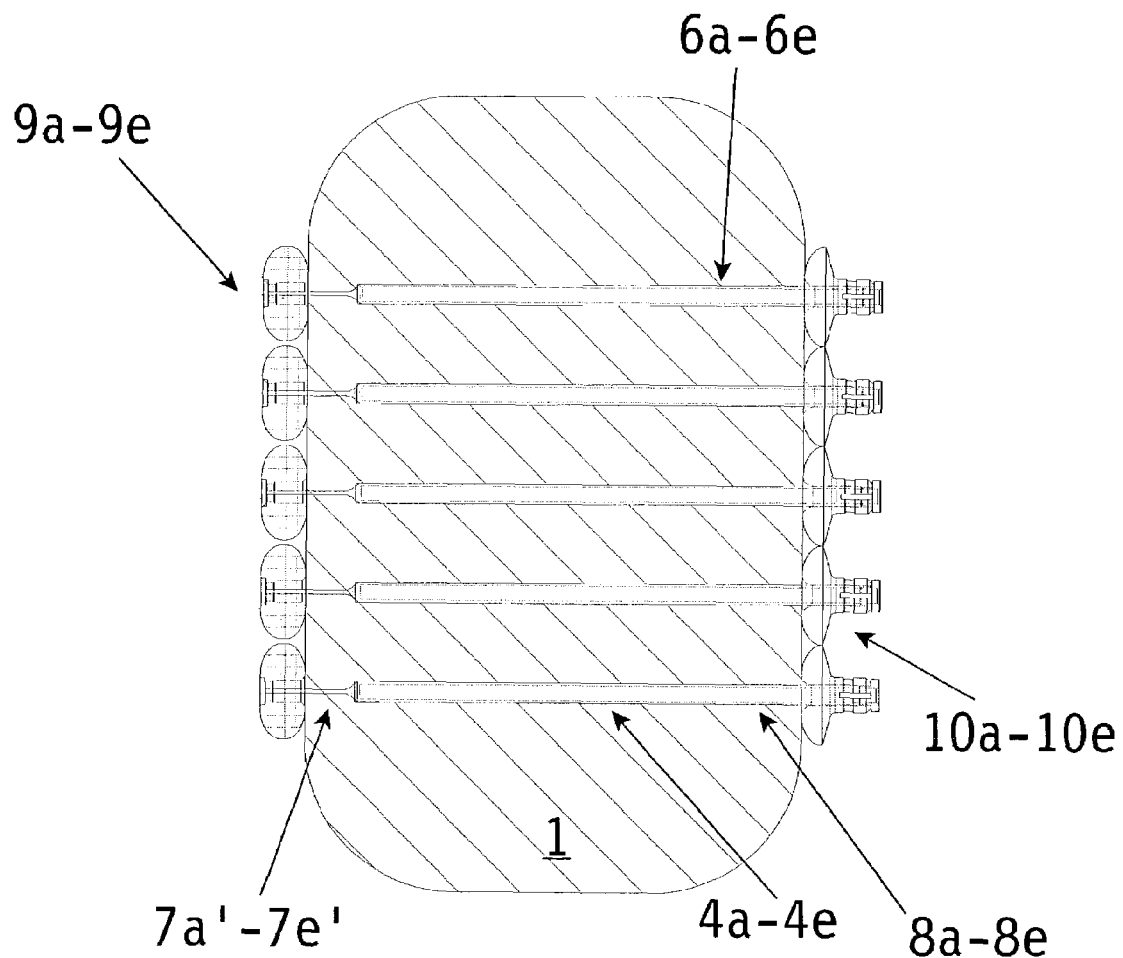
FIG. 3 shows another embodiment of the apparatus according to the invention in more detail.

In order to avoid or to reduce the forming of scars near the skin, which is penetrated by the trocar needle 2, 3 at the distal end therefrom (reference numeral 7a–7e in FIGS. 1G–1I) the needle 2a–2e as well as the guide tube 6a–6e can be provided with a distal end having a smaller diameter than the rest of the needle 2 and the guide tube 6a–6e. This is shown in FIG. 3, where each guide tube 6a–6e is provided with a distal end 7a'–7e' having a reduced diameter.

This embodiment of the apparatus according to the invention also requires a different sequence of inserting and positioning the guide tubes inside the breast 1. Once the hollow needles 2a–2e are inserted inside the body (breast 1), its smaller distal end is exposed outside the body at side 5a (FIG. 1). Then the guide tube 6a–6e having a similar smaller distal end 7a'–7e' is inserted via the proximal end of the open needle 2a–2e (reference numeral 5b in FIG. 1A). After removal of the open needle 2a–2e the smaller distal ends 7a'–7e' of each guide tube are connected to the fixing elements 9a–9e.

The smaller exit of the guide tube 6a–6e at its distal end through the skin of the patient reduces the discomfort of the patient during the subsequent radiation treatment therapy sessions and moreover reduces the forming of scars.

It should be noted that according to the abovementioned, various modifications may be obvious to a person skilled in the art. Such modifications are deemed to be within the scope of the invention.

The invention claimed is:

1. Method for temporarily inserting and positioning at least one energy emitting source in an animal body comprising at least the steps of:
   A inserting at least one hollow open needle having a proximal needle end and a distal needle end into the body so as to provide at least one channel in the body;
   B inserting a guide tube having a proximal guide tube end and a distal guide tube end to be inserted into the hollow open needle;
   C retracting the hollow open needle over the guide tube out of the body, while pulling the guide tube in position in the channel in the body;
   D fixating the guide tube with said proximal guide tube end relative to the body;
   E inserting via said proximal guide tube end a catheter tube having a closed distal catheter tube end and an open proximal catheter tube end with its distal catheter tube end until a predetermined depth into the guide tube and the body and fixating the catheter tube to the guide tube;
   F inserting via said proximal catheter tube end at least one energy emitting source into said catheter tube, and
   G after a predetermined period of time removing the at least one energy emitting source from the catheter tube, further characterized by
   H the at least one hollow open needle inserted at step A and said guide tube inserted at step B are inserted through a part of said body leaving both proximal and distal ends of said guide tube exposed outside either sides of said part of said body, and
   I fixing the guide tube with said distal guide tube end relative to the body.

2. Method according to claim 1, wherein step I is performed prior to step D.

3. Method according to claim 1, wherein said energy emitting source is inserted into the catheter tube by means of a flexible wire having a proximal wire end and a distal wire end.

4. Method according to claim 3, wherein said energy emitting source is connected at the distal wire end of said flexible wire.

5. Method according to claim 1, wherein said guide tube is non-collapsable between said proximal guide tube end and distal guide tube end.

6. An apparatus for temporarily inserting and positioning at least one energy emitting source in an animal body comprising at least:
   A a hollow open needle having a proximal needle end and a distal needle end to be inserted into the body, so as to provide a channel in the body;
   B a guide tube having a proximal guide tube end and a distal guide tube end to be inserted into the hollow open needle;
   C the hollow open needle being retractable from the body over the guide tube;
   D a first fixing element for fixating the guide tube with said proximal guide tube end relative to the body;
   E a catheter tube having a closed distal catheter tube end and an open proximal catheter tube end to be inserted with its distal catheter tube end until a predetermined depth into the guide tube and the body via said proximal guide tube end and fixating the catheter tube to the guide tube;
   F at least one energy emitting source for insertion into the catheter tube via said proximal catheter tube end and,
   G which at least one energy emitting source is removed after a predetermined period of time from the catheter tube, further characterized in that the hollow open needle and said guide tube are inserted through a part of said body leaving both proximal and distal ends of said guide tube exposed outside either sides of said part of said body, and
   a second fixing element for fixing the guide tube with said distal guide tube end relative to the body.

7. Apparatus according to claim 6, wherein said energy emitting source is inserted into the catheter tube by means of a flexible wire having a proximal wire end and a distal wire end.

8. Apparatus according to claim 7, wherein said energy emitting source is connected at the distal end of said flexible wire.

9. Apparatus according to claim 7, wherein said catheter tube is connected with said proximal catheter tube end to an afterloader apparatus.

10. Apparatus according to claim 9, wherein said flexible wire is connected with said proximal wire end to energy emitting source drive means of said afterloader apparatus.

11. Apparatus according to claim 6, wherein said catheter tube is made of a flexible material, like plastic.

12. Apparatus according to claim 6, wherein said guide tube is non-collapsable between said proximal guide end and said distal guide end.

13. Apparatus according to claim 6, wherein said distal end of said guide tube has a smaller diameter than the rest of said guide tube.

14. Apparatus according to claim 6, wherein at either sides of said part of the body a template is temporarily placed for positioning both proximal and distal ends of said hollow needle.

15. Apparatus according to claim 14, wherein both templates are mounted on one fixture.

16. Apparatus according to claim 6, wherein the first fixing element has means for fixation to the proximal end of the guide tube.

17. Apparatus according to claim 16, wherein said fixation means comprise two protruding parts extending parallel to each other and separated by two slits.

18. Apparatus according to claim 17, wherein said two protruding parts are urged away from each other due to the interaction between the slits and the legs of a tweezer-like device.

19. Apparatus according to claim 18, wherein each leg of said tweezer-like device is provided with a notch cooperating with each slit.

20. Apparatus according to claim 19, wherein said tweezer-like device is fastenable to the fixing element by means of a coupling device.

21. Apparatus according to claim 20, wherein the coupling device has one part of a click fit coupling, and another part of the click fit coupling is part of the fixing element.

22. Apparatus according to claim 20, wherein the coupling device has one part of a pressure and friction coupling and another part of the pressure and friction coupling is a part of the fixing element.

23. Apparatus according to claim 20, wherein the coupling device is one part of a key and lock coupling and another part of the key and lock coupling is part of the fixing element.

24. Apparatus according to claim 6, wherein the guide tube is made of a heat meltable material and the heat melted guide tube adheres to the fixing elements upon cooling in contact therewith.

25. Apparatus according to claim 6, wherein the energy emitting source is a high dose rate radioactive source.

26. Apparatus according to claim 6, wherein the energy emitting source is an activatable energy emitting source, which is operative between an activated and un-activated state.

27. Apparatus according to claim 26, wherein the activatable energy emitting source is an X-ray emitting device, a light-emitting device or a radiation emitting source, such as a HDR, PDR or LDR source.

28. Apparatus according to claim 6, wherein a dummy wire is to be inserted in the empty guide tube after the removal of the treatment device.

29. Apparatus according to claim 28, wherein said dummy wire is connected to the first fixing element.

* * * * *